United States Patent
Tupman et al.

(10) Patent No.: US 8,585,980 B2
(45) Date of Patent: Nov. 19, 2013

(54) ENHANCED PHOTO-CATALYTIC CELLS

(75) Inventors: David E. Tupman, Anna, TX (US); Wallace Weston Warren, Jefferson City, MO (US)

(73) Assignee: Puradigm, LLC, Las Vegas, NV (US)

( * ) Notice: Subject to any disclaimer, the term of this patent is extended or adjusted under 35 U.S.C. 154(b) by 0 days.

(21) Appl. No.: 13/225,812

(22) Filed: Sep. 6, 2011

(65) Prior Publication Data

US 2012/0141320 A1 Jun. 7, 2012

Related U.S. Application Data

(63) Continuation-in-part of application No. 13/115,546, filed on May 25, 2011.

(60) Provisional application No. 61/380,462, filed on Sep. 7, 2010.

(51) Int. Cl.
*A62B 7/08* (2006.01)
*B01J 19/12* (2006.01)

(52) U.S. Cl.
USPC .................. 422/122; 422/121; 422/186.3

(58) Field of Classification Search
USPC ...................... 422/121, 122, 186.3
See application file for complete search history.

(56) References Cited

U.S. PATENT DOCUMENTS

| | | | |
|---|---|---|---|
| 3,607,133 A | 9/1971 | Hirao et al. | |
| 4,230,571 A | 10/1980 | Dadd | |
| 5,078,971 A | 1/1992 | Matuda et al. | |
| 6,074,981 A | 6/2000 | Tada et al. | |
| 6,139,803 A | 10/2000 | Watanabe et al. | |
| 6,149,717 A | 11/2000 | Satyapal | |
| 6,194,346 B1 | 2/2001 | Tada et al. | |
| 6,248,235 B1 * | 6/2001 | Scott | 210/192 |
| 6,280,806 B1 | 8/2001 | Park et al. | |
| 6,391,269 B1 | 5/2002 | Yoshimatu | |
| 6,500,387 B1 | 12/2002 | Bigelow | |
| 6,524,536 B2 | 2/2003 | Newman et al. | |

(Continued)

FOREIGN PATENT DOCUMENTS

| | | |
|---|---|---|
| JP | 11276558 A | 10/1999 |
| JP | 2000254452 A | 9/2000 |

(Continued)

OTHER PUBLICATIONS

English Translation of Japanese Document No. JP 2001299881 A provided by the Industrial Property Digital Library: Suenaga, Yoshiaki; Deodorizing Device; Oct. 30, 2001.*

(Continued)

*Primary Examiner* — Kevin Joyner
(74) *Attorney, Agent, or Firm* — McAndrews, Held & Malloy, Ltd.

(57) ABSTRACT

According to an embodiment of the present invention, an apparatus for ionizing air includes a first reflector and a first target. The first reflector receives direct UV energy (from a UV emitter) and reflects it to form reflected UV energy. The first target has an inner face that also receives direct UV energy (from the UV emitter). The first target also has an outer face that receives the reflected UV energy from the first reflector. The faces of the first target are coated with a photo-catalytic coating. The first target may also have passages between the faces.

13 Claims, 9 Drawing Sheets

(56) References Cited

U.S. PATENT DOCUMENTS

| | | |
|---|---|---|
| 6,558,639 B1 | 5/2003 | Watanabe et al. |
| 6,752,957 B1 | 6/2004 | De Lasa et al. |
| 6,794,065 B1 | 9/2004 | Morikawa et al. |
| 6,902,653 B2 | 6/2005 | Carmignani et al. |
| 7,264,657 B2 | 9/2007 | Yuen |
| 7,329,313 B2 | 2/2008 | Wu |
| 7,371,351 B2 | 5/2008 | Goswami |
| 7,520,978 B2 | 4/2009 | Harbers |
| 7,704,913 B2 | 4/2010 | Tani et al. |
| 7,758,821 B2 | 7/2010 | Reisfeld et al. |
| 7,763,206 B2 | 7/2010 | Mole |
| 7,820,100 B2 | 10/2010 | Garfield et al. |
| 7,824,626 B2 | 11/2010 | Kwiatkowski |
| 8,012,412 B2 | 9/2011 | Normark et al. |
| 2002/0094298 A1 | 7/2002 | Monagan |
| 2003/0211022 A1 | 11/2003 | Gross et al. |
| 2004/0013583 A1 | 1/2004 | Burkhardt |
| 2004/0248075 A1 | 12/2004 | Yamaguchi et al. |
| 2005/0061656 A1 | 3/2005 | Benoit et al. |
| 2005/0063881 A1 | 3/2005 | Senne et al. |
| 2005/0186124 A1 | 8/2005 | Fink et al. |
| 2005/0191205 A1 | 9/2005 | Uslenghi et al. |
| 2005/0201907 A1 | 9/2005 | Wakamura |
| 2005/0220680 A1 | 10/2005 | Ma et al. |
| 2007/0194255 A1 | 8/2007 | Garcia et al. |
| 2007/0251812 A1 | 11/2007 | Hayman, Jr. |
| 2008/0031783 A1 | 2/2008 | Briggs et al. |
| 2008/0112845 A1 | 5/2008 | Dunn |
| 2008/0170971 A1 | 7/2008 | Bergeron et al. |
| 2008/0253941 A1 | 10/2008 | Wichers et al. |
| 2009/0035176 A1 | 2/2009 | Normark et al. |
| 2009/0152096 A1 | 6/2009 | Carlson |
| 2009/0166282 A1 | 7/2009 | Dong |
| 2009/0191100 A1 | 7/2009 | Deal |
| 2010/0092346 A1 | 4/2010 | Jeon |
| 2010/0143205 A1 | 6/2010 | Engelhard |
| 2010/0202932 A1 | 8/2010 | Danville |
| 2010/0303679 A1 | 12/2010 | Kim |
| 2012/0058006 A1 | 3/2012 | Tupman |

FOREIGN PATENT DOCUMENTS

| | | | |
|---|---|---|---|
| JP | 2001061947 A | | 3/2001 |
| JP | 2001-299881 A | | 10/2001 |
| JP | 2001299881 A | * | 10/2001 |
| JP | 2001340441 A | | 12/2001 |
| JP | 2004333035 A | | 11/2004 |
| JP | 2005152708 A | | 6/2005 |
| JP | 2005198846 A | | 7/2005 |
| JP | 2005-343427 A | | 12/2005 |

OTHER PUBLICATIONS

International Search Report and the Written Opinion, 11 pages, Jan. 23, 2012.

Intech Marketing, "Theairpurifiers.com," AirPura Air Purifier Design, Jan. 1, 2009, pp. 1-2.

Country Air, LLC, "Air Purifiers," Saver APR Object Cleaner, Jul. 2011, pp. 1-2.

International Search Report and Written Opinion in International application No. PCT/US2012/053831, dated Feb. 25, 2013. (13 pages).

* cited by examiner

ENHANCED PHOTO-CATALYTIC CELLS

RELATED APPLICATIONS

This application claims the benefit of U.S. Provisional Patent Application No. 61/380,462 filed on Sep. 7, 2010 and is a continuation-in-part of U.S. patent application Ser. No. 13/115,546, both of which are herein incorporated by reference in their entireties.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to methods and apparatuses for producing an enhanced ionized cloud of bactericidal molecules.

Photo-catalytic cells may be employed to produce bactericidal molecules—such as cluster ions—in airflow passing through the cells. The cells may be positioned to ionize air that may then be directed into a target environment, such as an enclosed space or room. Emerging molecules from the cells may have a bactericidal effect on various bacteria, molds or viruses which may be airborne in the room or may be on surfaces of walls or objects in the room.

Typically, such cells may be constructed with a target including or coated with a photo-catalytic coating and surrounding a broad spectrum ultra-violet ("UV") emitter. This combination can produce an ionized cloud of bactericidal molecules. The target may be coated with titanium dioxide as well as other elements. As air passes through or onto the target, UV energy striking the titanium dioxide may result in a catalytic reaction that may produce the desired cloud of bactericidal molecules within the airflow. These molecules—upon contact with any bacteria, mold, or virus—may kill them.

Effectiveness of a photo-catalytic cell may be dependent on the concentration of the bactericidal molecules. Furthermore, it may be desirable to have higher concentrations of cluster ions as compared to oxidizers. Consequently, it may be desirable for improved photo-catalytic cell designs to improve the efficiency of cluster ion generation.

BRIEF SUMMARY OF THE INVENTION

According to an embodiment of the present invention, an apparatus for ionizing air includes a first reflector and a first target. The first reflector receives direct UV energy (from a UV emitter) and reflects it to form reflected UV energy. The first target has an inner face that also receives direct UV energy (from the UV emitter). The first target also has an outer face that receives the reflected UV energy from the first reflector. The faces of the first target are coated with a photo-catalytic coating. The first target may also have passages between the faces. These passages may pass direct UV energy from the UV emitter to the first reflector. In an embodiment, the first reflector is a specular reflector or may have a curvature. The first target may also have a curvature. The curvature of the first reflector may be less than the curvature of the first target. The target may have a shape of a cylindrical, corrugated, or foil portion. The apparatus may also have a second reflector similar in some or all respects to the first reflector. The apparatus may also have a second target similar in some or all respects to the first target. In this case, the first and second targets may be separated by a gap between their leading edges and/or a gap between their trailing edges. It is also possible for the leading edges to touches and for the trailing edges to touches.

According to an embodiment of the present invention, an apparatus for ionizing air has a first reflector and a target. The first reflector receives direct UV energy from a first UV emitter and reflects this UV energy. The first reflector may be a specular reflector and may be parabolic. The target has a first face that also receives direct UV energy from the first UV emitter as well as the reflected UV energy from the first reflector. Furthermore, the target has a second face that receives direct UV energy from a second UV emitter. These faces are coated with a photo-catalytic coating. The apparatus may also have a second reflector that receives direct UV energy from the second UV emitter and reflects this UV energy towards the second face of the target.

According to an embodiment of the present invention, a method for ionizing air includes: receiving, at an inner face of a first target, UV energy from a UV emitter; responsively generating ions at a photo-catalytic coating on the inner face of the first target; reflecting, at a first reflector, UV energy from the UV emitter to form reflected UV energy; receiving, at an outer face of the first target, reflected UV energy from the first reflector; and responsively generating ions at a photo-catalytic coating on the outer face of the first target. The method may also include one or more of the following: passing, through a plurality of passages in the first target, UV energy from the UV emitter and towards the first reflector; passing an airflow over the inner and outer faces of the first target to carry the ions away from the first target; receiving, at an inner face of a second target, UV energy from a UV emitter; responsively generating ions at a photo-catalytic coating on the inner face of the second target; reflecting, at a second reflector, UV energy from the UV emitter to form reflected UV energy; receiving, at an outer face of the second target, reflected UV energy from the second reflector; responsively generating ions at a photo-catalytic coating on the outer face of the second target; passing, through a plurality of passages in the first target, UV energy from the UV emitter and towards the first reflector; passing, through a plurality of passages in the second target, UV energy from the UV emitter and towards the second reflector; passing an airflow over the inner and outer faces of the first target to carry the ions away from the first target; and passing the airflow over the inner and outer faces of the second target to carry the ions away from the second target.

According to an embodiment of the present invention, a method for ionizing air includes: receiving, at a first face of a target, ultra-violet ("UV") energy from a first UV emitter; responsively generating ions at a photo-catalytic coating on the first face of the target; reflecting, at a first reflector, UV energy from the first UV emitter to form reflected UV energy; receiving, at the first face of the target, reflected UV energy from the first reflector; and responsively generating ions at the photo-catalytic coating on the first face of the target. The method may also include one or more of the following: passing an airflow over the first face of the target to carry the ions away from the target; receiving, at a second face of the target, UV energy from a second UV emitter; responsively generating ions at a photo-catalytic coating on the second face of the target; reflecting, at a second reflector, UV energy from the second UV emitter to form reflected UV energy; receiving, at the second face of the target, reflected UV energy from the second reflector; responsively generating ions at the photo-catalytic coating on the second face of the target; and passing an airflow over the first and second faces of the target to carry the ions away from the target.

According to an embodiment of the present invention, an apparatus for ionizing air has a first foil target portion and a second foil target portion. Each of the foil target portions has passages and an inner face that receives direct UV energy from a UV emitter. The inner faces are coated with a photo-catalytic coating. The leading edges of the foil target portions may be touching or separated by a gap. Similarly, the trailing edges of the foil target portions may be touching or separated by a gap.

Figure 1:
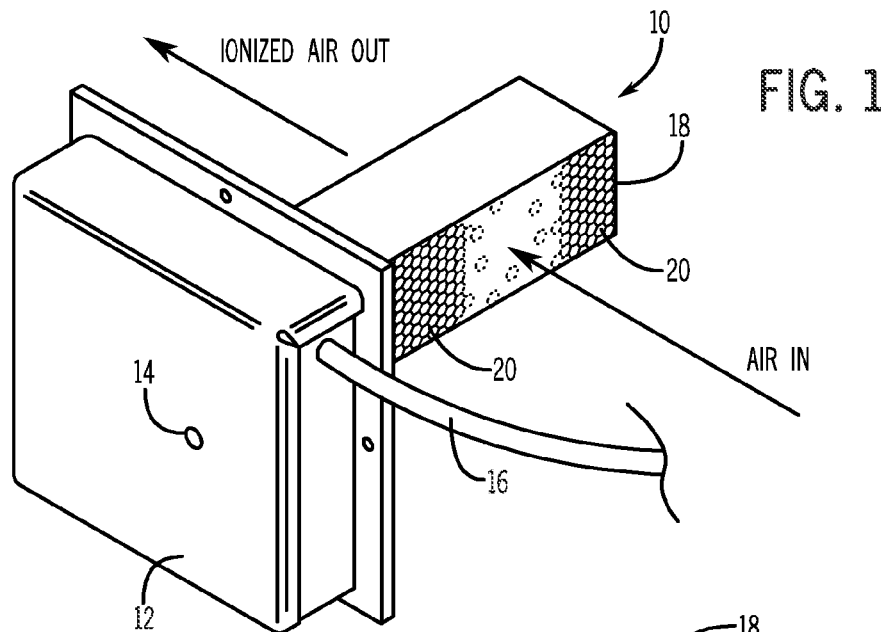
FIG. 1 shows a perspective view of a photo-catalytic cell, according to an embodiment of the present invention.

The foregoing summary, as well as the following detailed description of certain embodiments of the present invention, will be better understood when read in conjunction with the appended drawings. For the purposes of illustration, certain embodiments are shown in the drawings. It should be understood, however, that the claims are not limited to the arrangements and instrumentality shown in the attached drawings. Furthermore, the appearance shown in the drawings is one of many ornamental appearances that can be employed to achieve the stated functions of the system.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention. Various inventive features are described below that can be used independently of one another or in combination with other features.

Broadly, embodiments of the present invention generally provide a photo-catalytic cell in which one or more reflectors may be positioned to reflect UV energy and increase a proportion of emitted UV energy that strikes a target in the cell at high incident angles.

Figure 3:
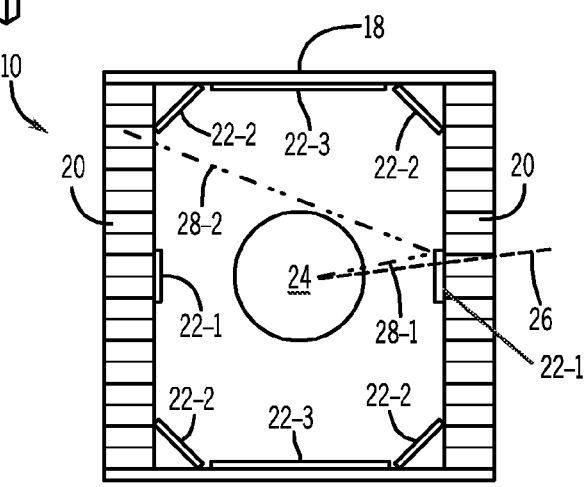
FIG. 3 shows a cross-sectional view of the photo-catalytic cell of FIG. 2 taken along the line 3-3, according to an embodiment of the present invention.
Figure 2:
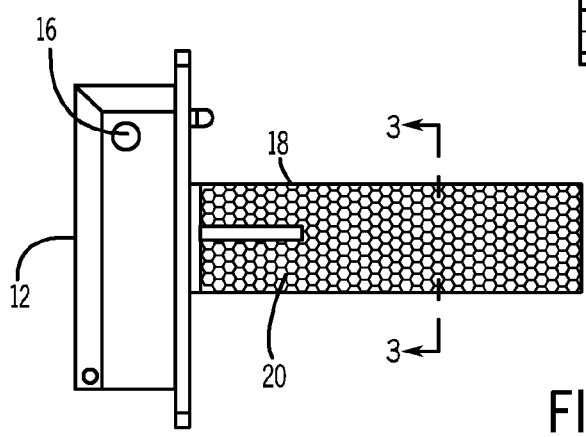
FIG. 2 shows a side elevation view of a photo-catalytic cell, according to an embodiment of the present invention.
Figure 4:
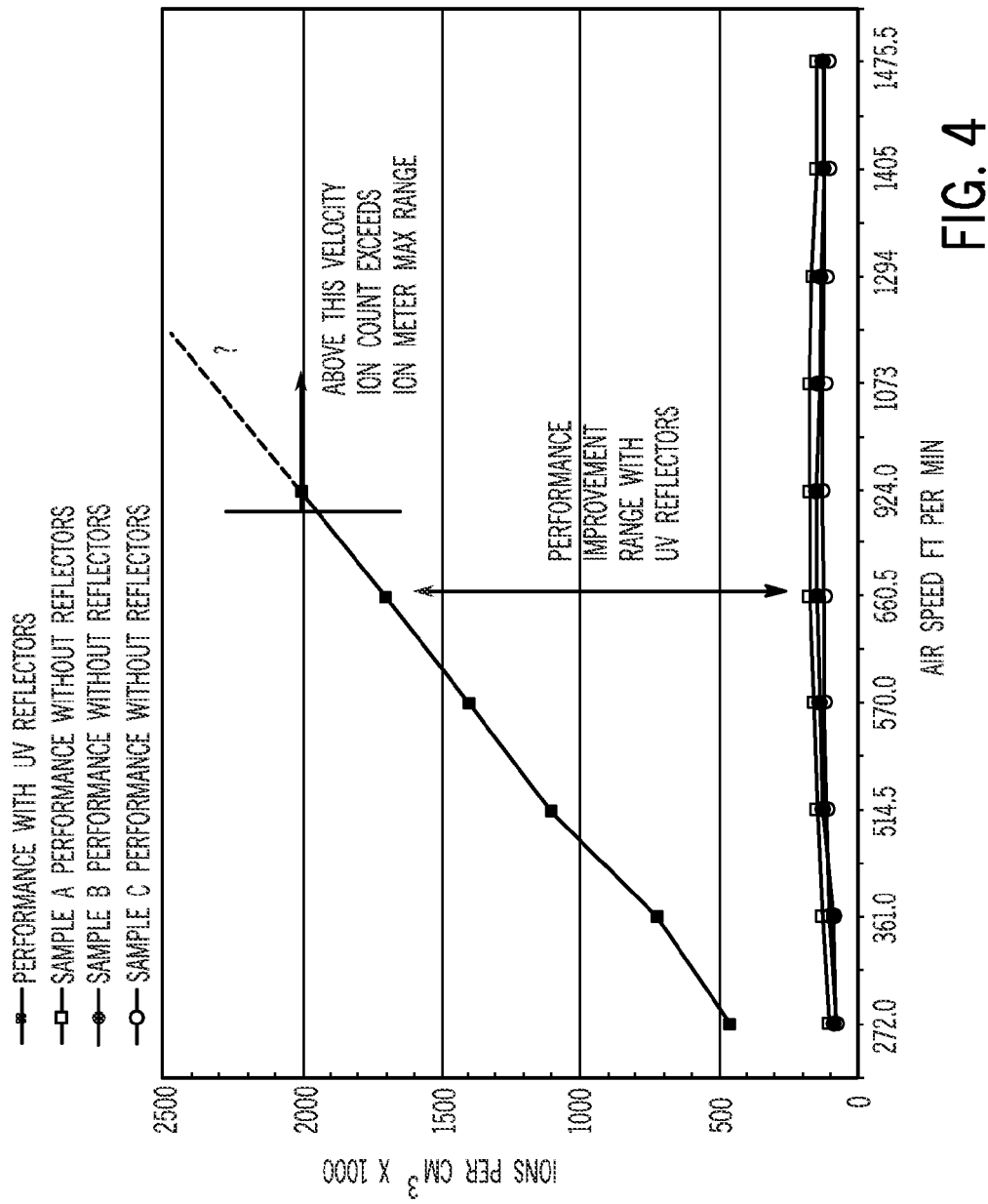
FIG. 4 shows a graph illustrating a difference in performance of a photo-catalytic cell with and without UV reflectors, according to an embodiment of the present invention.

Referring to FIGS. 1-3, a photo-catalytic cell 10 may include an electronics box 12, a light pipe indicator 14, a power cord 16, a chamber 18, honeycomb targets 20, UV reflectors (22-1, 22-2, and 22-3), and a UV emitter or lamp 24. The honeycomb targets 20 may be coated with titanium dioxide.

Airflow may pass across the honeycomb targets 20 while UV energy may be applied to the target 20 by the lamp 24. A photo-catalytic reaction may take place in the presence of the UV energy. The reaction may produce bactericidal molecules in the air.

Referring to FIG. 3, the efficacy of the UV reflectors 22-1 may be illustrated. If a reflector 22-1 is not present, an emitted ray 26 might pass through the honeycomb target 20 without impinging on the titanium dioxide. However, when one of the reflectors 22-1 is present, an illustrative emitted ray 28-1 of UV energy may impinge on the UV reflectors 22-1. The ray 28-1 may be reflected to become a reflected ray 28-2. It may be seen that the reflected ray 28-2 may impinge on a surface of the honeycomb target 20. It may be seen that a hypothetical unreflected ray 26, which might follow a path parallel to that of the ray 28-1, might pass through the honeycomb target 20 without impinging on the target 20. Thus, presence of the reflector 22-1 in the path of the ray 28-1 may result in avoidance of loss of the UV energy from the ray 28-1. The reflectors 22-1 may be relatively small as compared to the size of the honeycomb target 20. The small size (about 10% of the size of the target 20) may allow for minimal airflow obstruction. In spite of their relatively small size, the reflectors 22-1 may be effective because they may reflect virtually all of the (normally lost) UV energy that is emitted in a direction that is almost orthogonal (e.g., within ±5° of orthogonality) to the outer vertical plane of the honeycomb target 20. Hence, UV energy may pass through the honeycomb target 20 without touching the titanium dioxide surface. But by reflecting the UV rays onto the opposite side target matrix, that energy could be captured and utilized so as to add to the total ion count within the desired cloud of ionized molecules. In other words, the number of ions created by any incoming UV ray is proportional to the sine of the incident angle θ between the UV ray path and the titanium dioxide surface that a given ray is impacting, as illustrated by the following trigonometric relationships:

| For θ = 90° | Sin(θ) = 1 | Maximum energy gathered |
| For θ = 0° | Sin(θ) = 0 | Minimum energy gathered |

Reflectors 22-3 may be interposed between the lamp 24 and walls of the chamber 18. UV energy striking the reflectors 22-3 may be reflected onto the honeycomb target 20. Thus presence of the reflectors 22-3 may result in avoidance of loss of UV energy that might otherwise be absorbed or diffused by walls of the chamber 18. Similarly, reflectors 22-2 may be placed in corners of the chamber 18 to reflect UV energy onto the honeycomb target 20.

The reflectors 22-1, 22-2, and/or 22-3 may be constructed from material that is effective for reflection of energy with a wavelength in the UV range (e.g., about 184-255 nm). While soft metals such as gold and silver surfaces may be effective reflectors for visible light, their large grain size may make them less suitable than metallic surfaces with a small grain size (e.g., hard metals). Thus, hard metals such as chromium and stainless steel and other metals that do not readily oxidize may be effective UV reflectors and may be particularly effective for use as UV reflectors in a photo-catalytic cell. Material with a UV reflectivity of about 90% or higher may be suitable for use in the reflectors 22-1, 22-1 and/or 22-3. Lower reflectively produces lower effectiveness. To achieve the level of reflection required, it may be necessary to micro-polish or buff a selected materials reflective surface.

Reflecting surfaces of the reflectors 22 may be electrically conductive and/or grounded. Specifically, surface coatings (added for oxidation protection) like glass, clear plastics, or clear anodization (e.g., non-conductive) may diminish any performance enhancement of a photo-catalytic cell.

Also, reflecting surfaces of the UV reflector 22 may produce surface specular reflection. Specular reflection may be, for example, a mirror-like reflection of light in which a single incoming light ray is reflected into a corresponding single outgoing direction. Specular reflection is distinct from diffuse reflection, in which a single incoming light ray is reflected into a broad range of directions. Diffuse reflection may diminish performance enhancement of a photo-catalytic cell.

In an embodiment of the photo-catalytic cell 10, the reflectors 22-1, 22-2 and 22-3 may be chromium-plated plastic. Chromium-plated plastic may be a relatively low cost material with a relatively high degree of reflectivity for UV energy. So-called soft chrome, such as the plating used to produce a mirror-like finish that is seen on automobile chromed surfaces, may be employed.

It may be noted that there may be other cell shape designs which are not rectangular. For example, the cell 10 may be circular, tubular, or may have an otherwise complex shape. For these non-rectangular shaped cells, an optimum reflector design may be curved or otherwise non-flat in shape.

Figure 5:
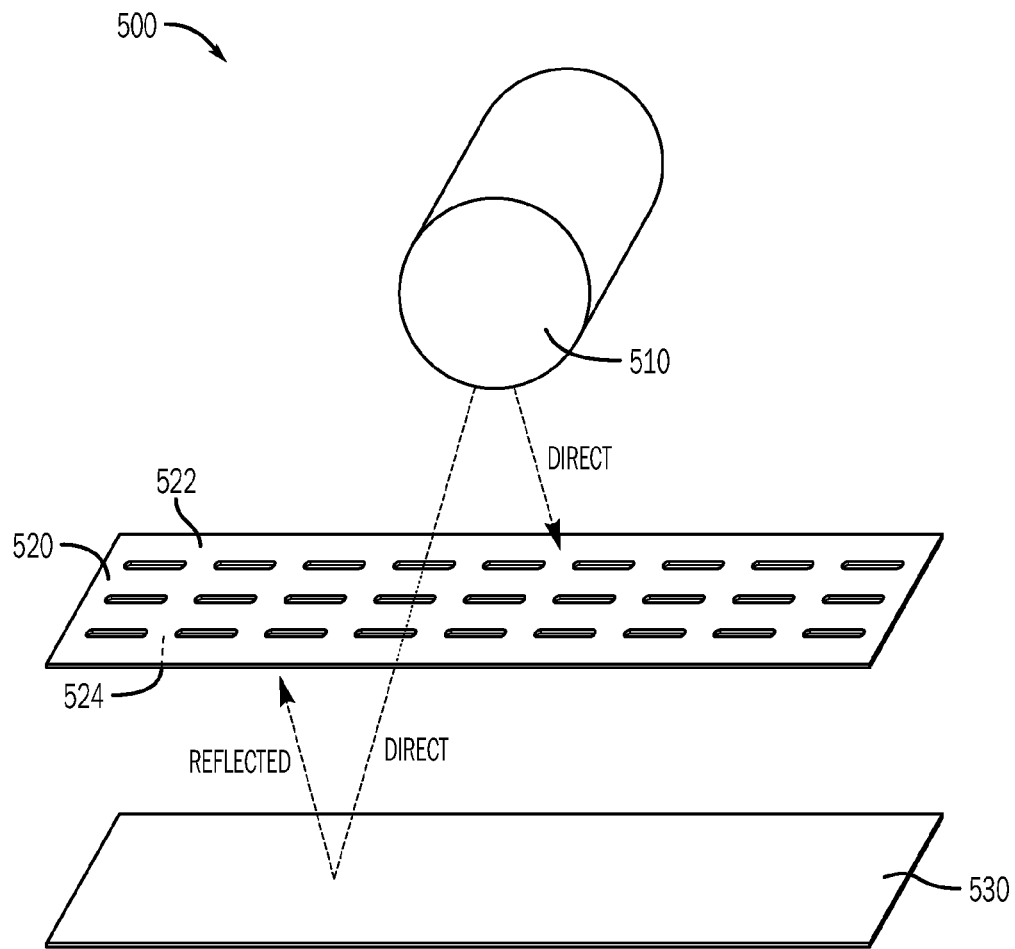
FIGS. 5-11 show various apparatuses for ionizing air, according to embodiments of the present invention.

Referring to FIG. 5, an apparatus 500 for ionizing air is shown according to an embodiment of the present invention. The apparatus 500 includes a UV emitter 510, a target 520, and a reflector 530.

The UV emitter 510 may emit direct UV energy (e.g., 184-255 nm wavelengths). The UV emitter 510 may be a lamp (e.g., fluorescent, LED, laser gas-discharge, etc.). The target 520 may have an inner face 522 and an outer face 524. The inner face 522 may be arranged to face or to receive direct UV energy from the UV emitter 510.

The reflector 530 may receive direct UV energy from the UV emitter 510. The target 520 may have passages between the inner and outer faces 522, 524. As an example, the passages may be slits (e.g., ½" long) or holes (e.g., ¼" diameter). Such slits may be horizontally arranged (as shown) or transversely arranged (e.g., from leading edge towards trailing edge). There may be a distance between each passage (e.g., ½" for the horizontal arrangement or ¾" for the transverse arrangement). The passages may be in rows. For example, the rows may be separated from each other by ½". The passages may have a thickness, such as the thickness of a nickel.

The direct UV energy may pass through these passages and towards the reflector 530. The reflector may reflect this direct UV energy, and the outer face 524 of the target 520 may be arranged to receive this reflected UV energy. The reflector 530 may include a specular reflector and may specularly reflect the UV energy. The specular reflector may be grounded.

The inner and outer faces 522, 524 of the target 520 may be coated with a photo-catalytic coating such as, for example, a coating that includes $TiO_2$ that facilitates the generation of ions in response to receiving the UV energy (direct and reflected).

Figure 6:
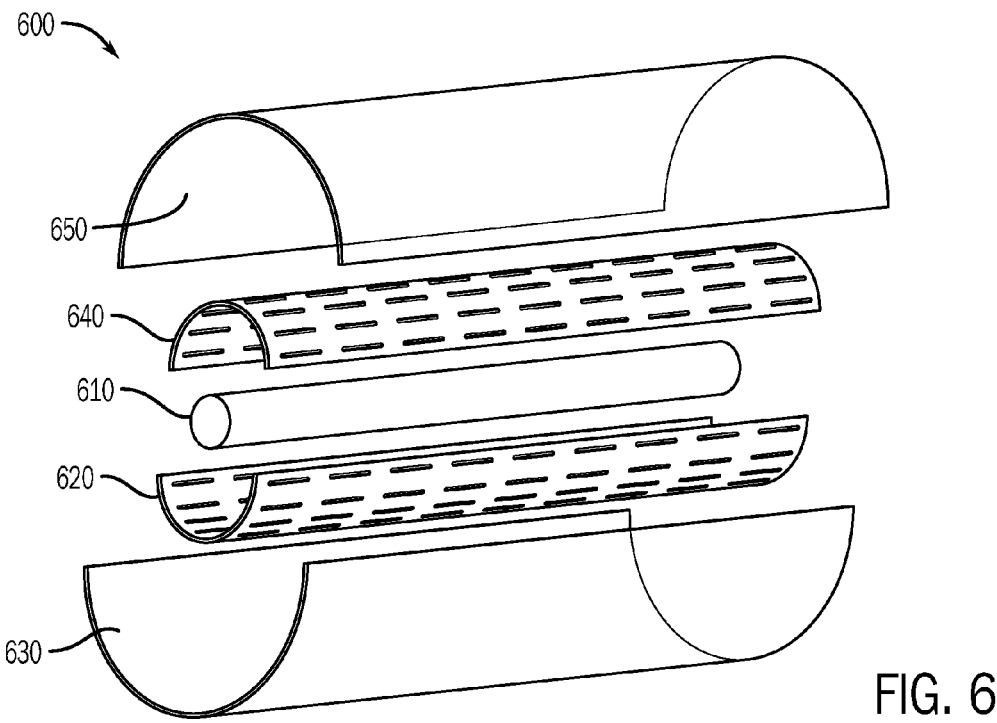

Referring to FIG. 6, an apparatus 600 for ionizing air is shown according to an embodiment of the present invention. The apparatus 600 may be, in many respects, similar to the apparatus 500. The apparatus 600 may include a UV emitter 610, a first target 620, a first reflector 630, a second target 640, and a second reflector 650. The second target 640 may be opposite the first target 620. The second reflector 650 may be opposite the first reflector 630.

Both targets 620, 640 may have inner and outer faces coated with a photo-catalytic coating to facilitate the generation of ions in response to receiving UV energy. Both reflectors 630, 650 may include specular reflectors. The inner faces of the targets 620, 640 may receive direct UV energy from the UV emitter 610. The reflectors 630, 650 may also receive direct UV energy from the UV emitter 510. For example, direct UV energy may pass through passages in the targets 620, 640 to reach the reflectors 630, 650. The reflected UV energy from the reflectors 630, 650 may be received at outer faces of the targets 620, 640.

The inner and outer faces of the targets 620, 640 may be coated with a photo-catalytic coating such as, for example, a coating that includes $TiO_2$ that facilitates the generation of ions in response to receiving the UV energy (direct and reflected).

One or both of the targets 620, 640 may have a curvature. For example, the target(s) 620, 640 may have a shape of a cylindrical portion. One or both of the reflectors 630, 650 may also have a curvature. The curvature of the target(s) 620, 640 may be greater than the curvature of the reflector(s) 630, 650.

The targets 620, 640 each may have a leading edge and a trailing edge. The leading edges may be upstream of an airflow from the trailing edges. The leading edge of the first target 620 may be separated from the leading edge of the second target 640 by a leading edge gap (as illustrated). Alternatively, the leading edges may be connected or abutting. Similarly, the trailing edge of the first target 620 may be separated from the trailing edge of the second target 640 by a trailing edge gap, or the trailing edges may be connected or abutting.

Figure 7:
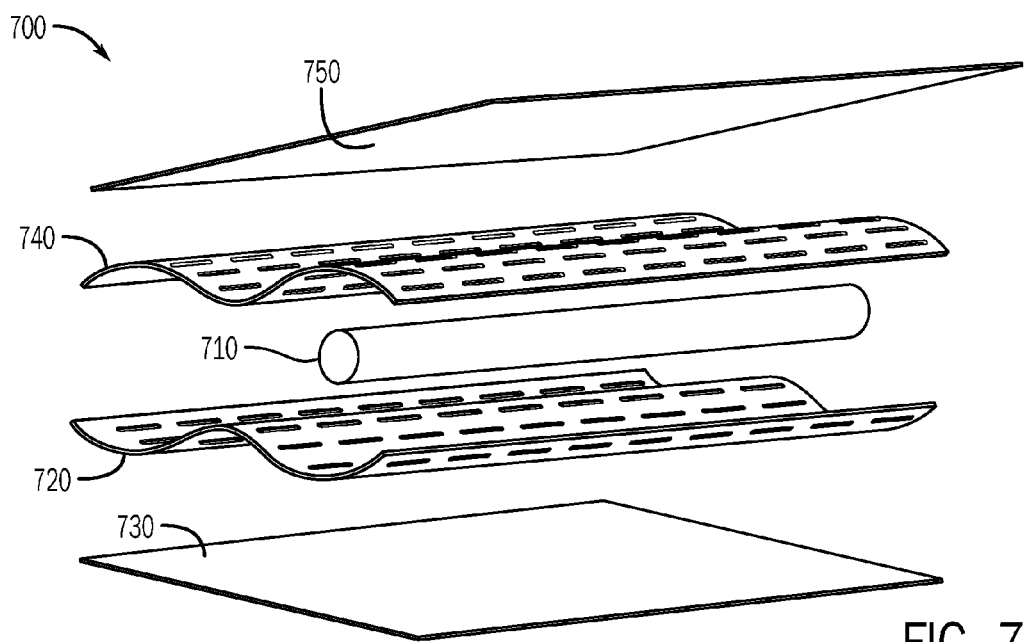
Figure 8:
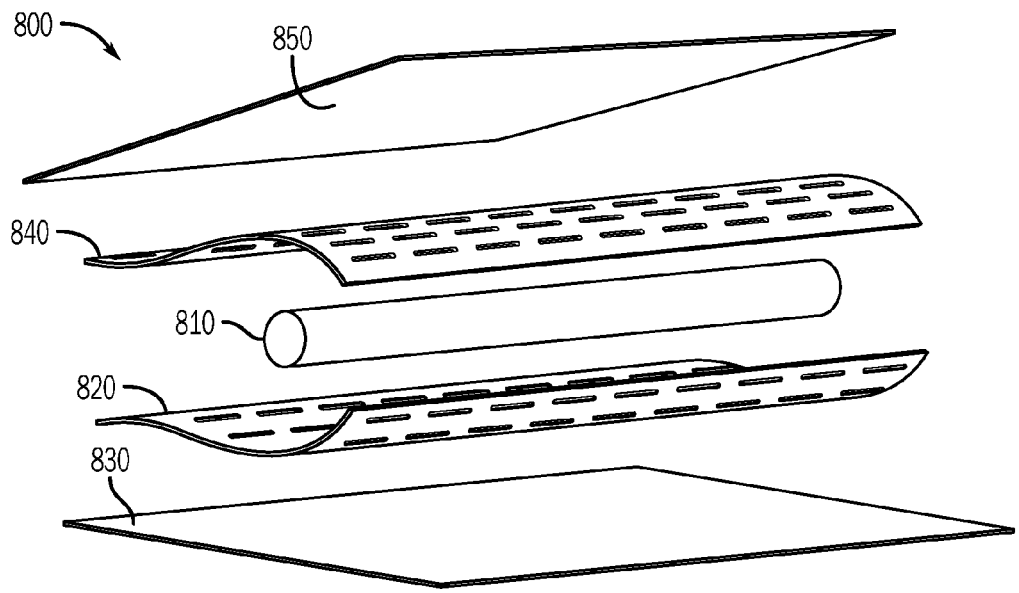

Referring to FIGS. 6-8, different target and reflector shapes are illustrated. The targets may have cylindrical portions (e.g., targets 620, 640 in FIG. 6). The targets may have corrugated portions (e.g., targets 720, 740 in FIG. 7). For example, a corrugated portion may have two peaks and two or three valleys. The targets may have foil portions (e.g., targets 820, 840 in FIG. 8). Other target shape variations are also possible. The shapes of the first and second targets may be different from each other.

The targets may have cylindrical portions (e.g., targets 620, 640 in FIG. 6). The targets may have corrugated portions (e.g., targets 720, 740 in FIG. 7). The targets may have foil portions (e.g., targets 820, 840 in FIG. 8). Other target shape variations are also possible. The shapes of the first and second targets may be different from each other.

The reflectors may be curved (e.g., reflectors 630, 650 in FIG. 6) or flat (e.g., reflectors 730, 750 in FIG. 7 or reflectors 830, 850 in FIG. 8). Other reflector shape variations are also possible. The shapes of the first and second reflectors may be different from each other.

Figure 10:
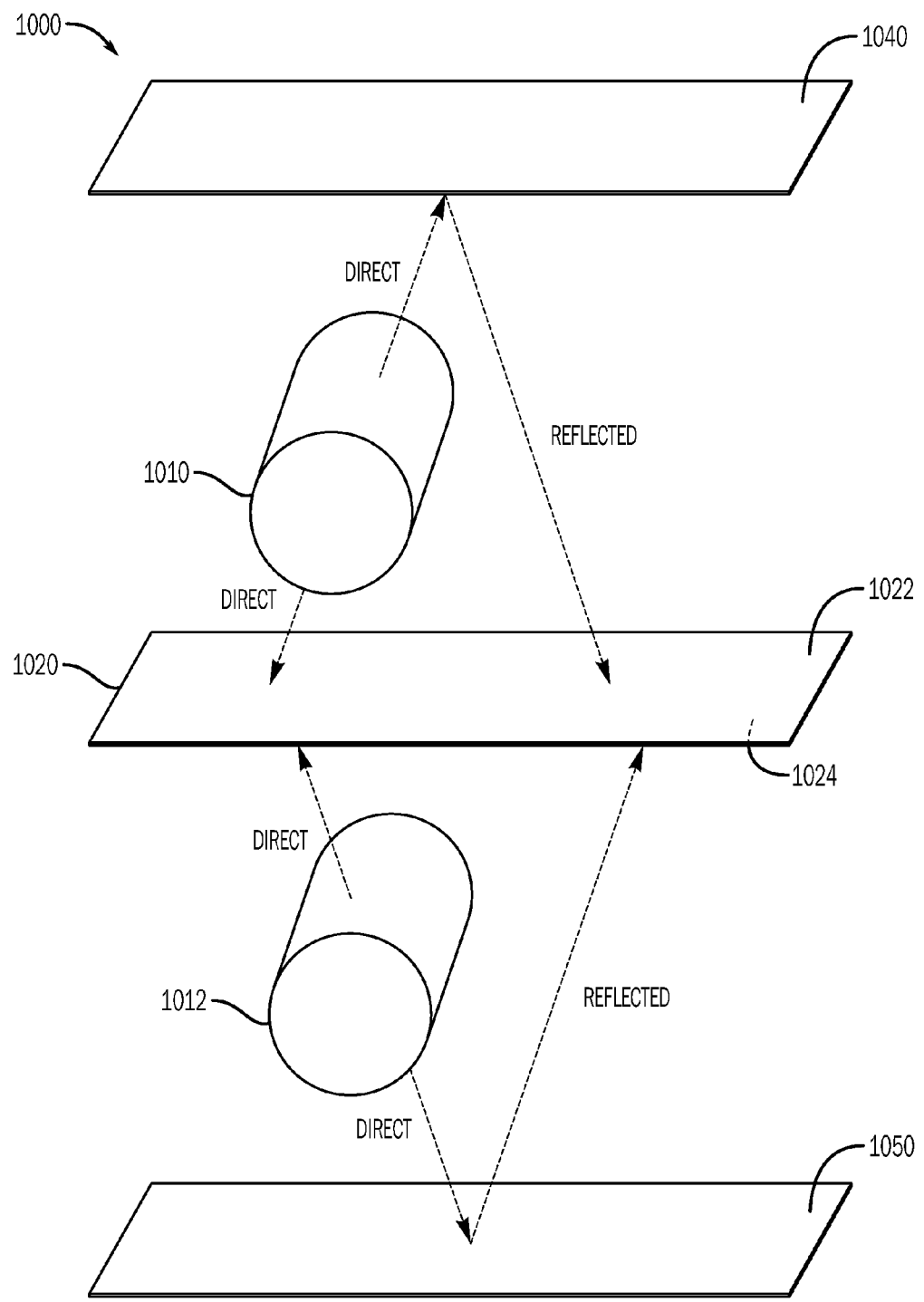

Referring to FIG. 10, an apparatus 1000 may have a first UV emitter 1010, a second UV emitter 1012, a target 1020, a first reflector 1040, and a second reflector 1050. The target may have a first face that is arranged to receive direct UV energy from the first UV emitter. The target may also have a second face arranged to receive direct UV energy from a second UV emitter. The faces of the target may be coated with a photo-catalytic coating.

Figure 11:
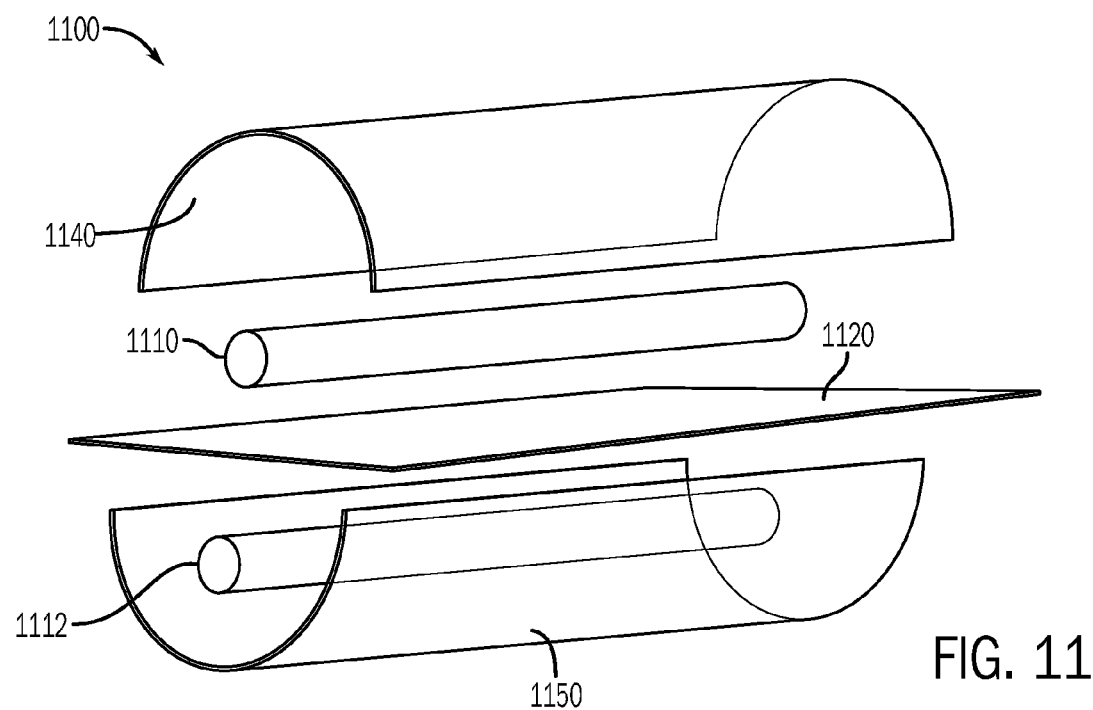

The first reflector may receive direct UV energy from the first UV emitter and reflect it towards the first face of the target. The second reflector may receive direct UV energy from the second UV emitter and reflect it towards the second face of the target. The reflectors may be specular reflectors and may be grounded. The reflectors may be parabolic (see FIG. 11). A parabolic reflector may be helpful to reflect UV energy in a direction orthogonal to the target 1020.

Figure 12:
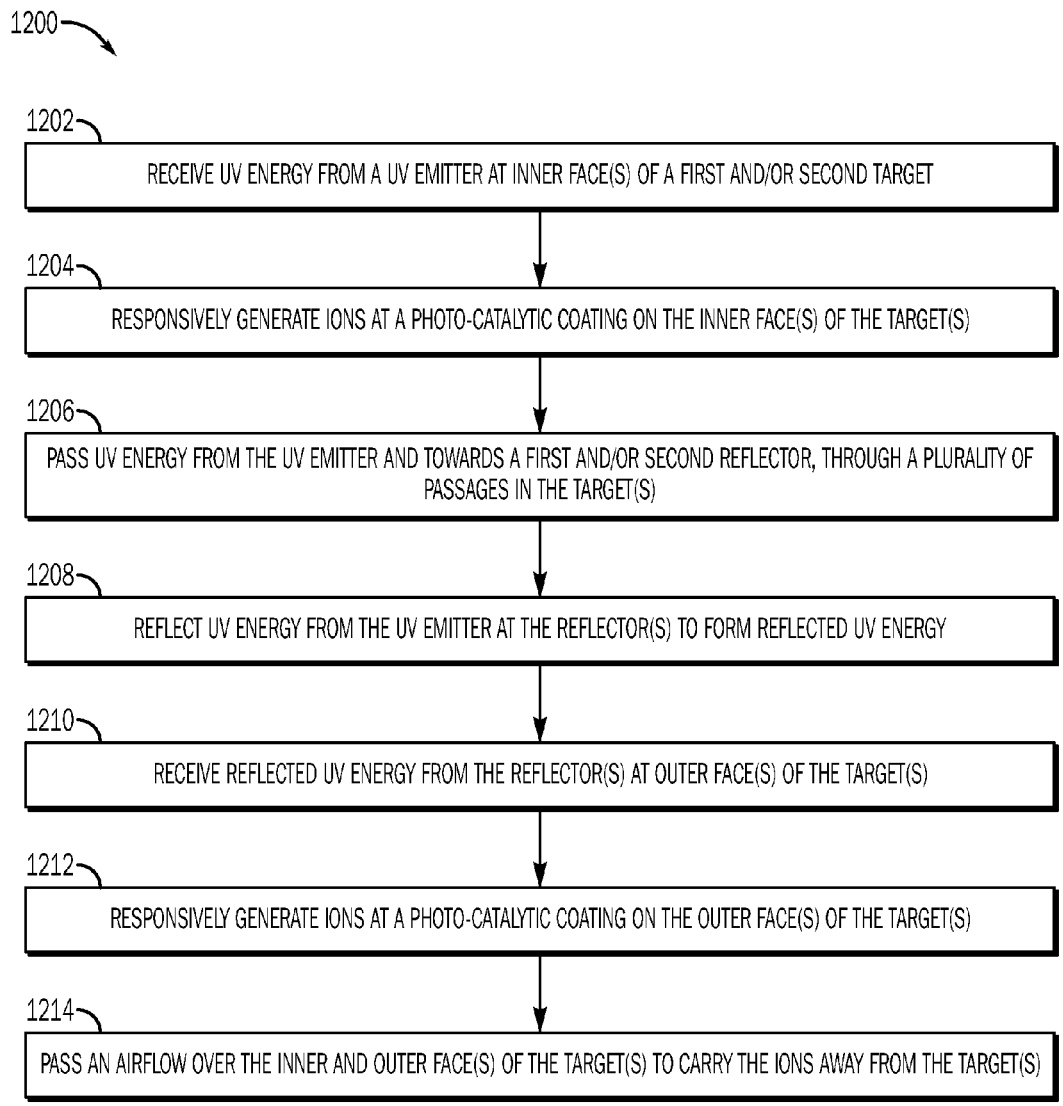
FIG. 12 shows a flowchart of a method for ionizing air, according to an embodiment of the present invention.

FIG. 12 shows a flowchart 1200 of a method for ionizing air, according to an embodiment of the present invention. The flowchart 1200 may be performable, for example, with an apparatus such as the ones shown in FIGS. 5-8. Furthermore, the flowchart 1200 may be performable in a different order, or some steps may be omitted according to design or preferences.

At step 1202, UV energy is received from a UV emitter at inner face(s) of a first and/or second target. At step 1204, ions are responsively generated at a photo-catalytic coating on the inner face(s) of the target(s). At step 1206, UV energy is passed from the UV emitter and towards a first and/or second reflector, through a plurality of passages in the target(s). At step 1208, UV energy is reflected from the UV emitter at the reflector(s) to form reflected UV energy. At step 1210, reflected UV energy is received from the reflector(s) at outer face(s) of the target(s). At step 1212, ions are responsively generated at a photo-catalytic coating on the outer face(s) of the target(s). At step 1214, an airflow is passed over the inner and outer face(s) of the target(s) to carry the ions away from the target(s).

Figure 13:
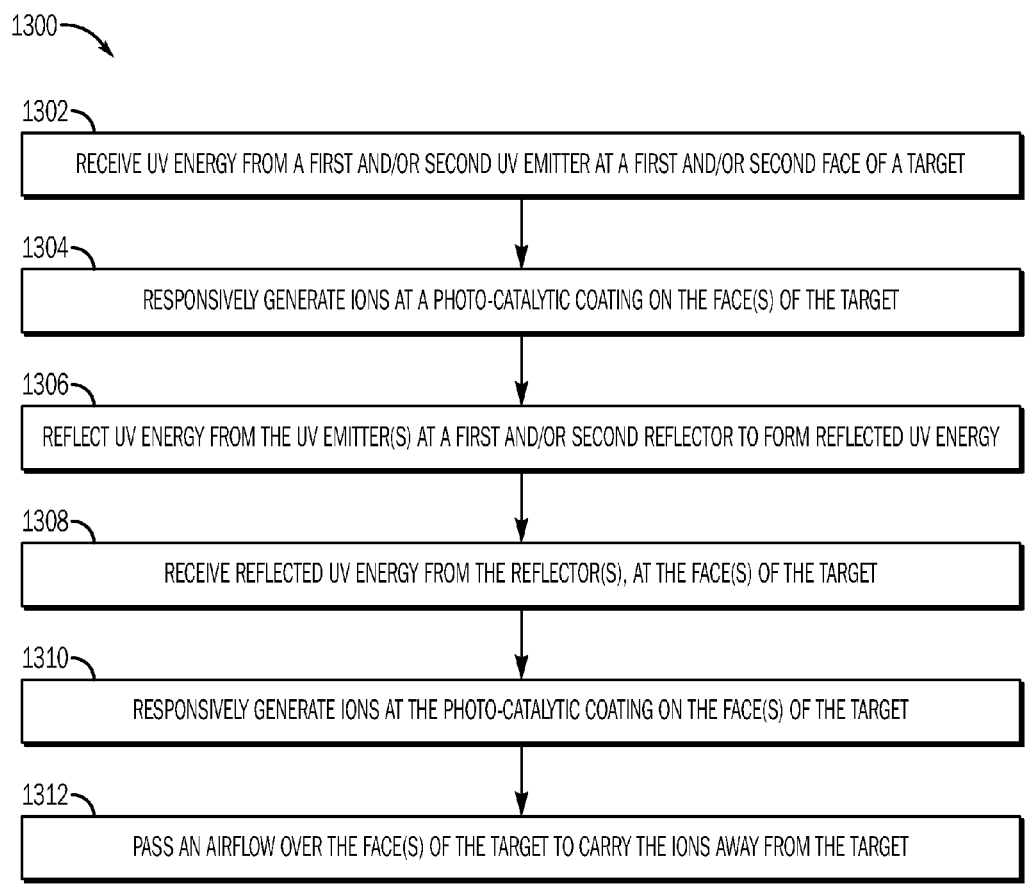
FIG. 13 shows a flowchart of a method for ionizing air, according to an embodiment of the present invention.

FIG. 13 shows a flowchart 1300 of a method for ionizing air, according to an embodiment of the present invention. The flowchart 1300 may be performable, for example, with an apparatus such as the ones shown in FIGS. 10 and 11. Furthermore, the flowchart 1300 may be performable in a different order, or some steps may be omitted according to design or preferences.

At step 1302, UV energy is received from a first and/or second UV emitter at a first and/or second face of a target. At step 1304, ions are responsively generated at a photo-catalytic coating on the face(s) of the target. At step 1306, UV energy is reflected from the UV emitter(s) at a first and/or second reflector to form reflected UV energy. At step 1308, reflected UV energy is received from the reflector(s), at the face(s) of the target. At step 1310, ions are responsively generated at the photo-catalytic coating on the face(s) of the target. At step 1312, an airflow is passed over the face(s) of the target to carry the ions away from the target.

Figure 9A:
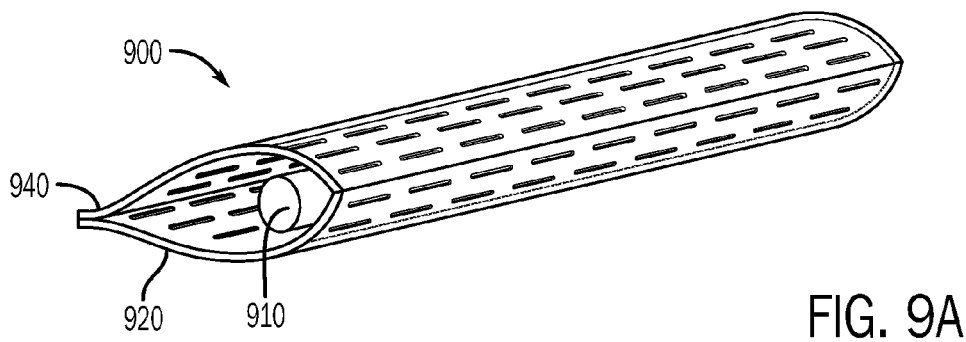
Figure 9B:
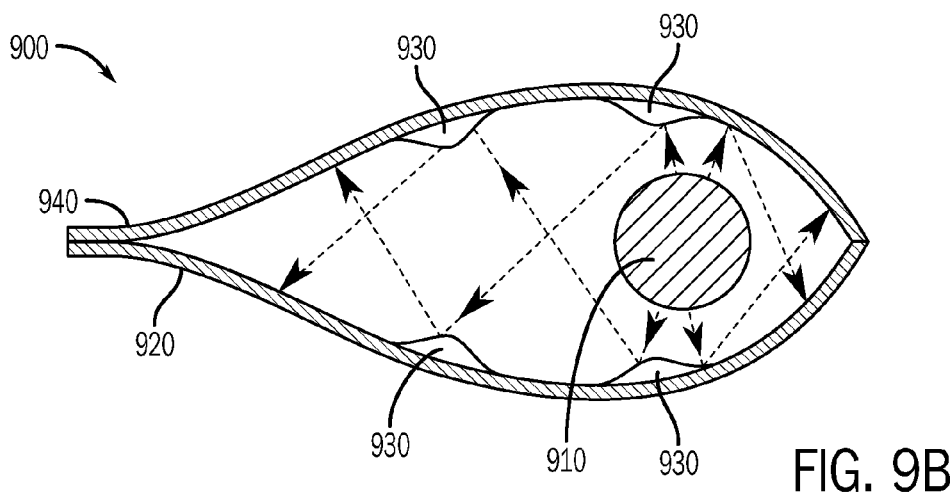

FIGS. 9A and 9B show an apparatus 900 for ionizing air, according to an embodiment of the present invention. The apparatus 900 may be similar, in some respects, to apparatus 800 shown in FIG. 8. The apparatus 900 may include a UV emitter 910, a first foil target portion 920, and a second foil target portion 940. One or each of the foil target portions 920, 940 may have an inner face arranged to receive direct UV energy from the UV emitter 910. One or each of the foil target portions 920, 940 may have a plurality of passages and may be coated with a photo-catalytic coating on the inner face. The leading edges of the foil portions may be touching (e.g., abutting, connecting, integrated) or may be separated by a leading edge gap. The trailing edges of the foil portions may abut or may be separated by a trailing edge gap. The apparatus 900 may also have one or more reflectors 930 arranged on or near the inner faces of the first or second foil target portions. Such reflectors 930 may also be used in combination with other reflectors, such as those shown in FIGS. 5-8.

Turbulence may tend to destroy cluster ions. A foil-shaped target may be useful to reduce turbulence as airflow passes over. Other turbulence-reducing techniques may include the use of an air straightener upstream from a leading edge of a target. Furthermore, higher airflow speeds may be useful for efficiently generating cluster ions but not oxidizers. The foil design may accelerate the airflow to improve the efficiency of this process.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. An apparatus for ionizing air, the apparatus comprising:
a first reflector arranged to:
   receive direct UV energy from a UV emitter; and
   reflect the direct UV energy to form reflected UV energy;
a first target including:
   an inner face arranged to face towards the UV emitter and receive direct UV energy from the UV emitter;
   an outer face arranged to face away from the UV emitter and receive the reflected UV energy from the first reflector;
   a plurality of passages between the inner and outer faces of the first target, wherein the plurality of passages of the first target is arranged to pass direct UV energy from the UV emitter and to the first reflector, and wherein each of the plurality of passages is surrounded by the first target;
   a leading edge; and
   a trailing edge;
a photo-catalytic coating on the inner and outer faces of the first target;
a second reflector opposite the first reflector and arranged to:
   receive direct UV energy from the UV emitter; and
   specularly reflect the direct UV energy to form reflected UV energy;
a second target opposite the first target and including:
   an inner face arranged to face towards the UV emitter and receive direct UV energy from the UV emitter;
   an outer face arranged to face away from the UV emitter and receive the reflected UV energy from the second reflector;
   a plurality of passages between the inner and outer faces of the second target, wherein the plurality of passages of the second target is arranged to pass direct UV energy from the UV emitter and to the second reflector, and wherein each of the plurality of passages is surrounded by the second target;
   a leading edge; and
   a trailing edge;
a photo-catalytic coating on the inner and outer faces of the second target; and
wherein:
   the inner face of the first target faces towards the inner face of the second target;
   the outer face of the first target faces away from the outer face of the second target; and
   both of the leading edges of the first and second targets are arranged to be upstream from both of the trailing edges of the first and second targets when an airflow is passed along the apparatus.

2. The apparatus of claim 1, wherein the first reflector comprises a specular reflector.

3. The apparatus of claim 1, wherein the first target comprises a curvature.

4. The apparatus of claim 3, wherein the first reflector comprises a curvature.

5. The apparatus of claim 4, wherein the curvature of the first target is greater than the curvature of the first reflector.

6. The apparatus of claim 4, wherein the first target comprises a first foil portion.

7. The apparatus of claim 1, wherein the first reflector and the second reflector comprise specular reflectors.

8. The apparatus of claim 1, wherein:
the first target comprises a curvature; and
the second target comprises a curvature.

9. The apparatus of claim 8, wherein:
the first reflector comprises a curvature; and
the second reflector comprises a curvature.

10. The apparatus of claim 9, wherein:
the curvature of the first target is greater than the curvature of the first reflector; and
the curvature of the second target is greater than the curvature of the second reflector.

11. The apparatus of claim 8, wherein:
a leading edge of the first target and a leading edge of the second target are separated by a leading edge gap; and
a trailing edge of the first target and a trailing edge of the second target are separated by a trailing edge gap.

12. The apparatus of claim 8, wherein:
a leading edge of the first target touches a leading edge of the second target; and
a trailing edge of the first target touches a trailing edge of the second target.

13. The apparatus of claim 8, wherein:
the first target comprises a first foil portion; and
the second target comprises a second foil portion.

\* \* \* \* \*